US009028516B2

(12) United States Patent
Palmer et al.

(10) Patent No.: US 9,028,516 B2
(45) Date of Patent: May 12, 2015

(54) SURGICAL INSTRUMENT AND METHOD OF USE FOR RELEASING SOFT TISSUE

(71) Applicant: Del Palma Orthopedics, Columbia City, IN (US)

(72) Inventors: Andrew K. Palmer, Eastham, MA (US); Dale Dellacqua, Bloomington, IN (US); Jeffrey A. Farris, Berne, IN (US)

(73) Assignee: Del Palma Orthopedics, Columbia City, IN (US)

( * ) Notice: Subject to any disclaimer, the term of this patent is extended or adjusted under 35 U.S.C. 154(b) by 0 days.

(21) Appl. No.: 14/054,560

(22) Filed: Oct. 15, 2013

(65) Prior Publication Data

US 2014/0039533 A1    Feb. 6, 2014

Related U.S. Application Data

(62) Division of application No. 12/210,302, filed on Sep. 15, 2008, now Pat. No. 8,579,930.

(51) Int. Cl.
*A61B 17/32* (2006.01)

(52) U.S. Cl.
CPC . *A61B 17/320016* (2013.01); *A61B 17/320036* (2013.01); *A61B 2017/320052* (2013.01)

(58) Field of Classification Search
CPC ............... A61B 17/320036; A61B 17/0218; A61B 17/320016; A61B 17/1146; A61B 17/00234; A61B 17/320783; A61B 17/3211; A61B 1/313; A61B 2018/00946; A61B 2018/24; A61B 19/306; A61B 2017/320052
USPC ........... 30/152, 173, 314, 317, 320, 335, 338, 30/294, 162, 286, 51, 282, 90.4, 62, 63, 30/171; 606/170, 171, 167, 79, 45, 180, 606/190, 172, 159, 148, 150; 600/562–572, 600/185, 214, 210, 211, 213, 183, 461; 112/295, 298, 299, 80.55–80.71
See application file for complete search history.

(56) References Cited

U.S. PATENT DOCUMENTS 2,569,080 A    9/1951   Trimble et al.
5,253,659 A   10/1993   McNamara (Continued)

FOREIGN PATENT DOCUMENTS

DE    29521451 U1    5/1997
WO     9742887 A    11/1997

OTHER PUBLICATIONS

Partial International Search Report for corresponding PCT application PCT/US2009/056653 mailed Dec. 10, 2009.

(Continued)

*Primary Examiner* — Jocelin Tanner
(74) *Attorney, Agent, or Firm* — Heslin Rothenberg Farley & Mesiti, P.C.

(57) ABSTRACT

A surgical instrument for use in releasing soft tissue within the human body. The surgical instrument has a handle with proximal and distal ends with a tube connected to the distal end. The surgical instrument also includes a blade member that slidingly engages the tube moving along the length of the tube to cut soft tissue. Further included in the surgical instrument is a guard member that is attached to the blade member. The guard member has a hood portion and a capture portion. The hood portion is connected to the blade member with the distally positioned capture portion acting to displace surrounding tissue while capturing certain soft tissue structures resulting in the blade member being in operative position to cut and release the soft tissue. A surgical instrument kit including a plurality of modular surgical instruments and method for releasing soft tissue using the surgical instrument are also disclosed.

10 Claims, 7 Drawing Sheets

(56) References Cited

U.S. PATENT DOCUMENTS

| | | | |
|---|---|---|---|
| 5,306,284 A * | 4/1994 | Agee et al. ............... 606/170 |
| 5,318,582 A | 6/1994 | Chow |
| 5,353,812 A | 10/1994 | Chow |
| 5,366,465 A | 11/1994 | Mirza |
| 5,387,222 A | 2/1995 | Stickland |
| 5,437,662 A | 8/1995 | Nardella |
| 5,480,408 A | 1/1996 | Chow |
| 5,569,283 A * | 10/1996 | Green et al. ............... 606/170 |
| 5,752,972 A | 5/1998 | Hoogeboom et al. |
| 5,782,850 A | 7/1998 | Ro |
| 5,827,312 A | 10/1998 | Brown |
| 5,893,861 A | 4/1999 | Yumoto |
| 5,908,433 A * | 6/1999 | Eager et al. ............... 606/170 |
| 5,957,944 A | 9/1999 | Khuri et al. |
| 6,755,815 B2 | 6/2004 | Schultz |
| 6,972,027 B2 | 12/2005 | Fallin et al. |
| 7,739,799 B2 | 6/2010 | Van Deursen |
| 2006/0149267 A1 | 7/2006 | Nordt |
| 2006/0178682 A1 | 8/2006 | Boehlke |
| 2006/0190021 A1 | 8/2006 | Hausman et al. |
| 2007/0288043 A1 * | 12/2007 | Rehnke ............... 606/170 |

OTHER PUBLICATIONS

Complete International Search Report and Written Opinion for corresponding international application No. PCT/US2009/056653 mailed Apr. 9, 2010.

International Preliminary Report on Patentability for corresponding PCT application No. PCT/US2009/056653, mailed Mar. 15, 2011.

* cited by examiner

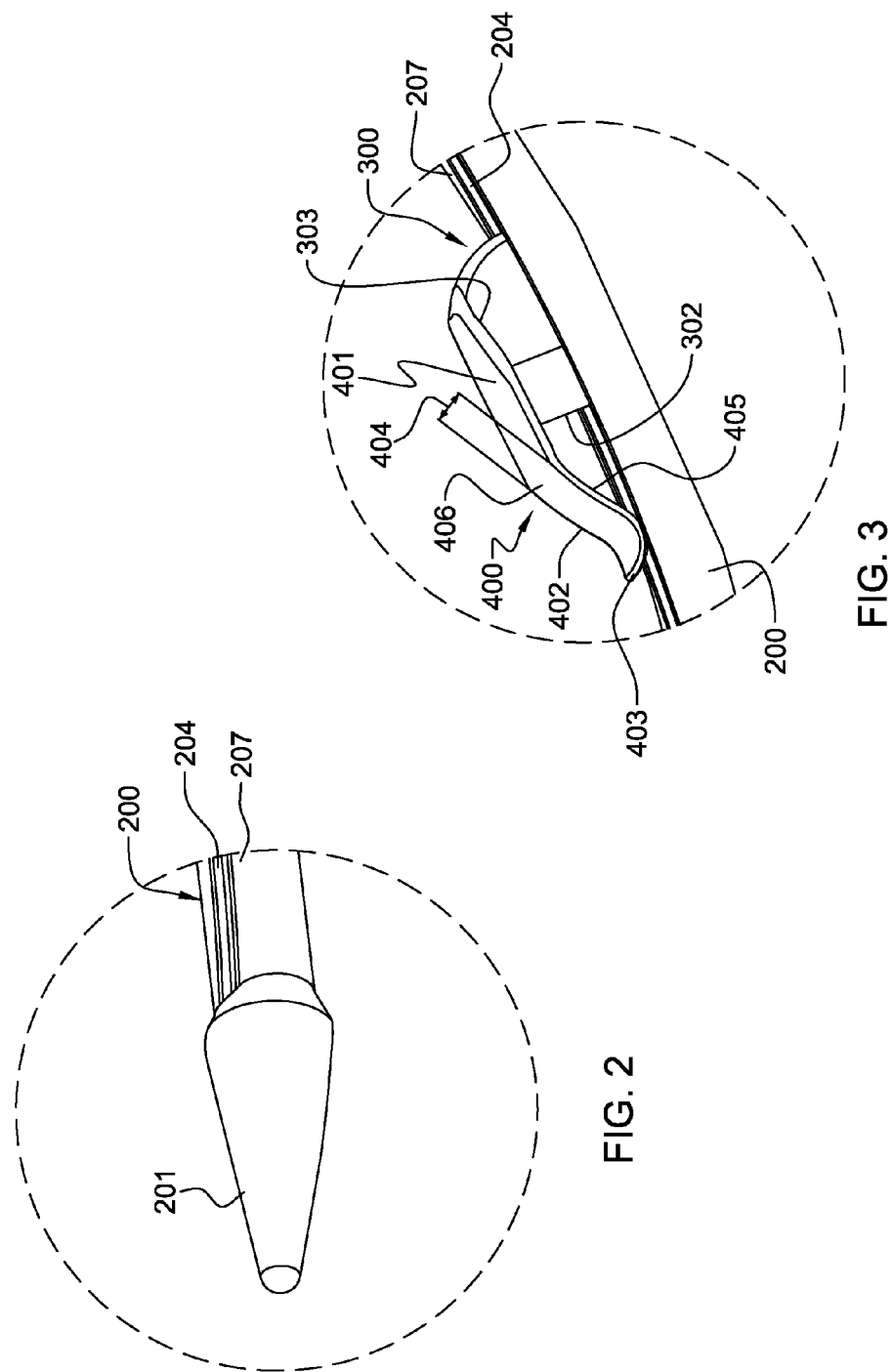

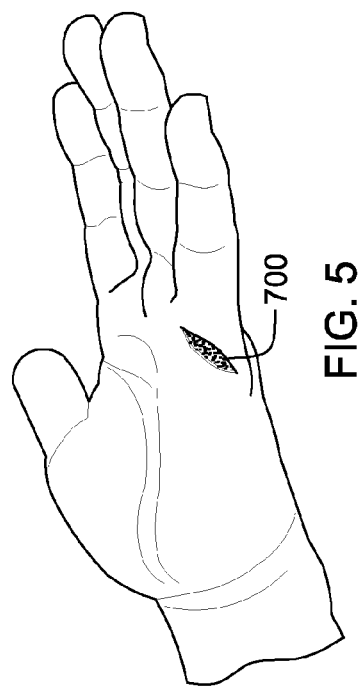
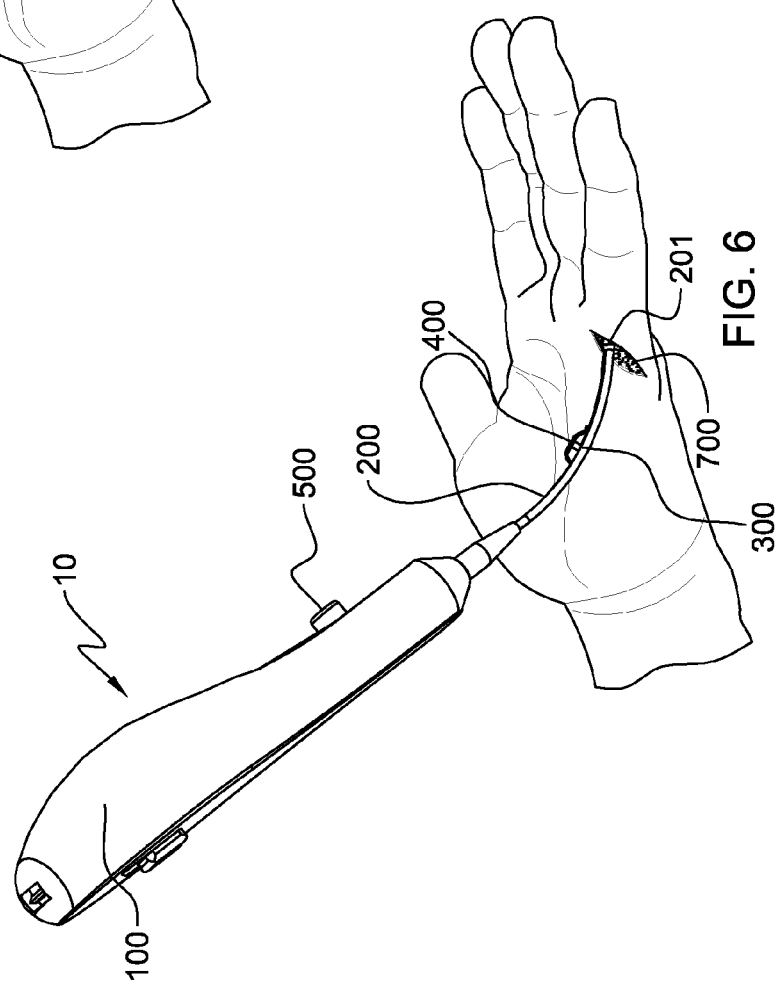

SURGICAL INSTRUMENT AND METHOD OF USE FOR RELEASING SOFT TISSUE

CROSS-REFERENCE TO RELATED APPLICATIONS

This application is a divisional of U.S. application Ser. No. 12/210,302 filed Sep. 15, 2008, now U.S. Pat. No. 8,579,930 which is hereby incorporated herein by reference in its entirety.

TECHNICAL FIELD

The present invention relates to the field of surgery, and more particularly, to surgical instruments and surgical methods for performing the release of constricted soft tissue or stenotic tissue within the body of a patient.

BACKGROUND OF THE INVENTION

Constriction of soft tissue within the body is a problem that affects people of all ages. For example, stenosing tendovaginitis, or trigger finger as the condition is commonly known, is an abnormal condition affecting the flexor tendons of the hand and affects people of all ages. The problem involves the tendon system of the hand and can range from a simple nuisance to completely disabling the function of the hand. The tendon system of the hand involves an extremely intricate and finely matched pulley system to allow each finger joint to move through a complete forceful arc of motion. The pulley system and tendon system dysfunction when a finger develops triggering (trigger finger). The mismatch or dysfunction causes a stenosis or tightening, this can be related to the tendon or the pulley. More specifically, the greatest excursion of the tendon occurs at the A-1 pulley and it is this pulley which is typically addressed by treatment. The causes of trigger finger as well as with other stenotic soft tissue scenarios includes overuse, inflammatory condition, diabetes and trauma.

Several non-surgical methods for treating constricted soft tissue, including trigger finger, are well known in the art, including splinting and steroid injection. Surgical treatment is designed to release the constricted soft tissue. For the example, with the trigger finger malady, the goal of releasing the A-1 pulley is achieved by cutting or removing part of the stenotic tissue. The surgery procedure may be performed in the operating room or an office setting using many different tools. Endoscopes, trigger release devices with fixed blades, finely pointed needles and even open surgical techniques with standard scalpels or scissors are currently the type of procedures and instrumentation used. Problems with the current surgical techniques include multiple incisions or entry wounds to the hand, the ongoing risk to adjacent neurological or vascular structures due to the proximity of the target soft tissue. For the example, with trigger finger surgical treatments, post-operative complications may include damage to the adjacent digital artery or digital nerve.

Accordingly, developing a new surgical instrument device and a corresponding surgical method to decrease the likelihood of intraoperative complications when releasing soft tissue and resultant lessened morbidity, would be desirable.

SUMMARY OF THE INVENTION

The present invention satisfies the need for an improved surgical instrument used to release the soft tissue of patients suffering from physical symptoms resulting from constricted or stenotic tissue and the need for an improved method of using a surgical instrument to treat constricted soft tissue in a patient.

The present invention provides in one aspect, a surgical instrument for releasing soft tissue that has a handle that includes proximal and distal ends with a longitudinal axis that extends between these ends. The surgical instrument also has a tube that includes a first end and a second end with a longitudinal axis extending between these two ends. The first end is shaped to assist with the insertion of the surgical instrument into the human body with the second end constructed to attach to the distal end of the handle. The surgical instrument further includes a blade member. The blade member is made to slide and move along the longitudinal axis of the tube to release adjacent soft tissue.

The present invention provides in another aspect, a surgical instrument for cutting soft tissue that includes a handle having both proximal and distal ends and a longitudinal axis extending between these ends. The surgical instrument also has a substantially hollow tube that has a first end and a second end with a longitudinal axis extending between these two ends. The first end is shaped to assist in inserting the surgical instrument into the human body. The second end is constructed to attach to the distal end of the handle. The surgical instrument further includes a blade member that is built to slide and move along the longitudinal axis of the substantially hollow tube to release the patient's soft tissue. The guard member is also part of the present surgical instrument invention and has a hood portion and a capture portion. The hood portion is connected to the blade member with the capture portion being positioned distal to the blade member to move away surrounding tissue when the blade member moves relative to the substantially hollow tube. The surgical instrument also has an actuator that is operationally connected to the blade member. When the actuator is actuated the blade member moves along the longitudinal axis of the substantially hollow tube to cut soft tissue after the surgical instrument has been inserted into the human body.

The present invention provides in yet another aspect, a method for releasing soft tissue within a patient that includes the step of surgically creating an opening in the skin of the patient that is proximate to the soft tissue to be released. The method includes the step of inserting a surgical instrument into the opening that has a handle having proximal and distal ends and a longitudinal axis that extends between the ends. The surgical instrument also has a tube that includes a first end and a second end with a longitudinal axis extending between these ends. The first end of the tube is made to assist with the insertion of the surgical instrument into the patient and the second end of the tube is constructed to be attached to the distal end of the handle. The surgical instrument also includes a blade member that is configured to slide and move relative to the tube along the tube's longitudinal axis. The method also includes the step of advancing the tube element of the surgical instrument into the opening of the patient to position the first end of the tube adjacent the target soft tissue. A further step of the method is to actuate or move the blade member along the longitudinal axis of the tube, engaging the soft tissue and placing the blade member in an operable position for the further step of cutting the soft tissue with the blade member to release the constricted soft tissue.

The present invention provides in another aspect, a surgical instrument kit for releasing soft tissue. The kit includes a plurality of surgical instruments. Each of the plurality of surgical instruments have a handle that includes a proximal end and distal end with a longitudinal axis extending between the ends. Each of the plurality of surgical instruments also include a tube having a first end and a second end with a longitudinal axis extending between these two ends. The first end is made to facilitate inserting the surgical instrument into the human body with the second end being constructed to attach to the distal end of the handle. Each of the plurality of surgical instruments also include a blade member that is made to slide and move relative to the tube along the tube's longitudinal axis. In addition, each of the plurality of surgical instruments have a guard member that is made with a hood portion and a capture portion. The hood portion is connected to the blade member with the capture portion being positioned distal to the blade member to displace and protect surrounding tissue when the blade member is moved along the longitudinal axis of the tube. Each of the plurality of surgical instruments may also include an actuator that is operationally connected to the blade member so that when the button member is actuated, the blade member moves along the tube's longitudinal axis of the tube to cut the constricted soft tissue within the human body.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

FIG. 2 is an enlarged side elevational view of a first end of a tube of the surgical instrument of FIG. 1, in accordance with an aspect of the present invention;

FIG. 3 is an enlarged perspective view of a blade member with attached guard member disposed within the tube of the surgical instrument of FIG. 1, in accordance with an aspect of the present invention;

FIG. 5 is a perspective view of a human hand following a surgical incision being made on the palmar side of a hand, in accordance with an aspect of the present invention;

FIG. 6 is a perspective view of the human hand showing the insertion of the tube of the surgical instrument of FIG. 1 into the incision on the palmar side of the hand, in accordance with an aspect of the present invention;

DETAILED DESCRIPTION FOR CARRYING OUT THE INVENTION

Figure 1:
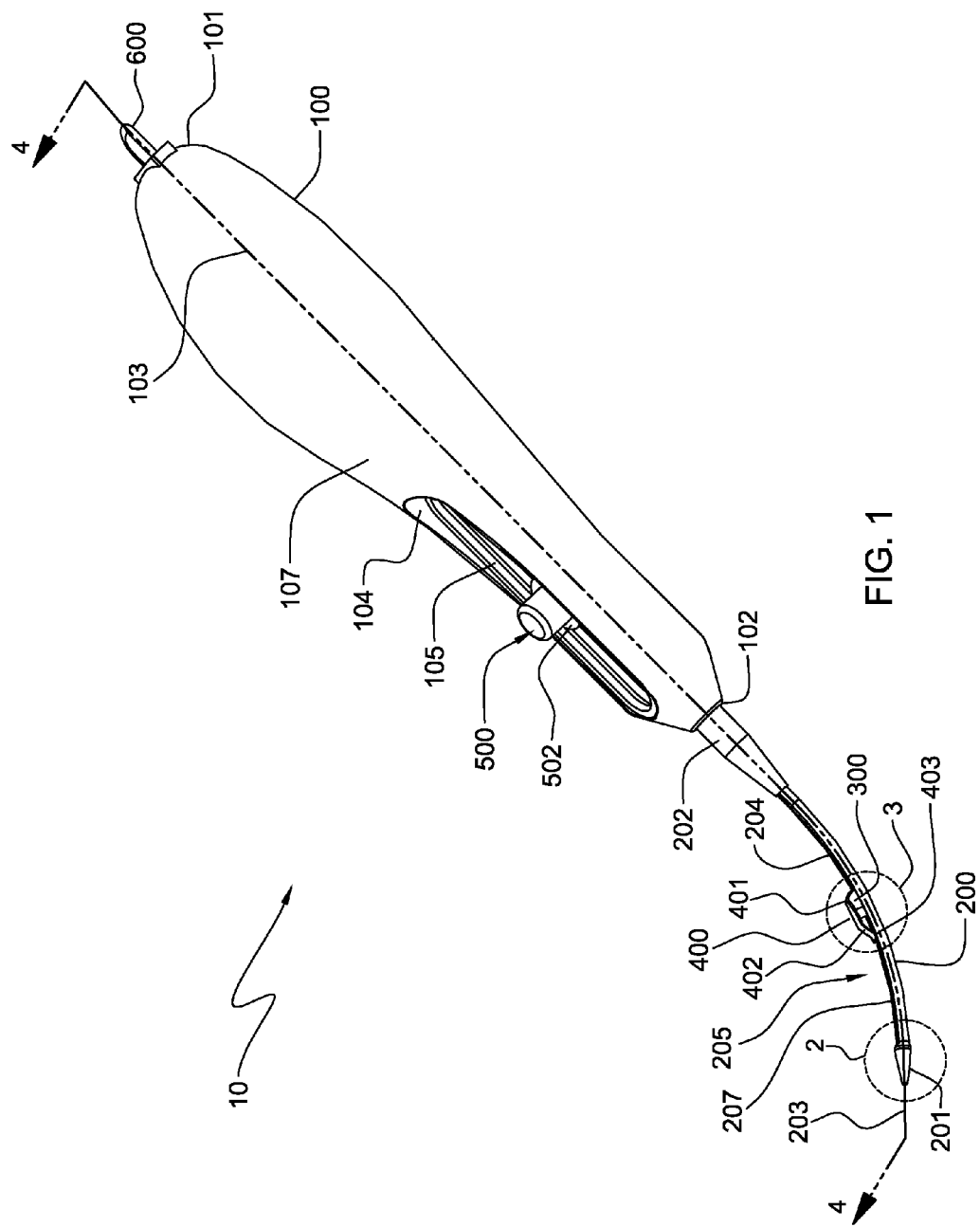
FIG. 1 is a perspective view of one embodiment of a surgical instrument used for releasing soft tissue in the body, in accordance with an aspect of the present invention.

Generally stated, disclosed herein is a surgical instrument for use to perform subcutaneous soft tissue release surgical procedures. The surgical instrument typically has a handle, a tube, a blade member with a connected guard member and an actuator to control the movement of the blade member. Also, described herein is a method for using the surgical instrument to release percutaneous soft tissue within the human body. Further, described is a surgical instrument kit with modular components including handles, tubes and blade members for use to release soft tissue within the human body. The invention or surgical device will generally be referred to herein as a "surgical instrument" or simply "instrument" for ease of discussion. Further, the use of the term "button member" herein should not in any way be interpreted as limiting the function of the element to having to be depressed or inserted into a hole or loop to operate. The term "button member" was used herein solely to describe a knob-like member or actuator and such term was not intended to limit or restrict in any way the element's function in the disclosed invention. In addition, the embodiments of the invention as described herein will typically be used in surgeries involving the releasing or cutting of soft tissue structures, but it should be understood by one skilled in the art that the surgical instrument is in no way limited to just such surgeries. The invention may be used for a number of other surgical procedures and methods including, but not limited to the cutting of bones, muscles, connective tissue, vascular structures, nervous tissue, fascia releases and organ dissection. In this regard, the surgical instrument may be used to cut other constricted tissue in all parts of the body. As noted, constricted soft tissue may effect in some manner, tendons, ligaments, nerves, veins, arteries, bones and muscles as well as other tissue types and organs. Therefore, it is contemplated that the disclosed surgical instrument may be used to treat stenosing tenosynovitis of the dorsal compartment of the wrist, carpal tunnel syndrome, cubital tunnel syndrome, tarsal tunnel syndrome, plantar fascitis and any other generically constricted or entrapped above tissues/structures in the body.

In this detailed description and the following claims, the words proximal, distal, anterior, posterior, medial, lateral, superior and inferior are defined by their standard usage for indicating a particular part of the human body or instrument according to the relative disposition of the particular part or directional terms of reference. For example, "proximal" means the portion of the instrument nearest the torso, while "distal" indicates the portion of the instrument farthest from the torso. As for directional terms, "anterior" is a direction towards the front side of the body, "posterior" means a direction towards the rear-side of the body, "medial" means towards the midline of the body and "lateral" is a direction towards the sides or away from the midline of the body.

Figure 4:
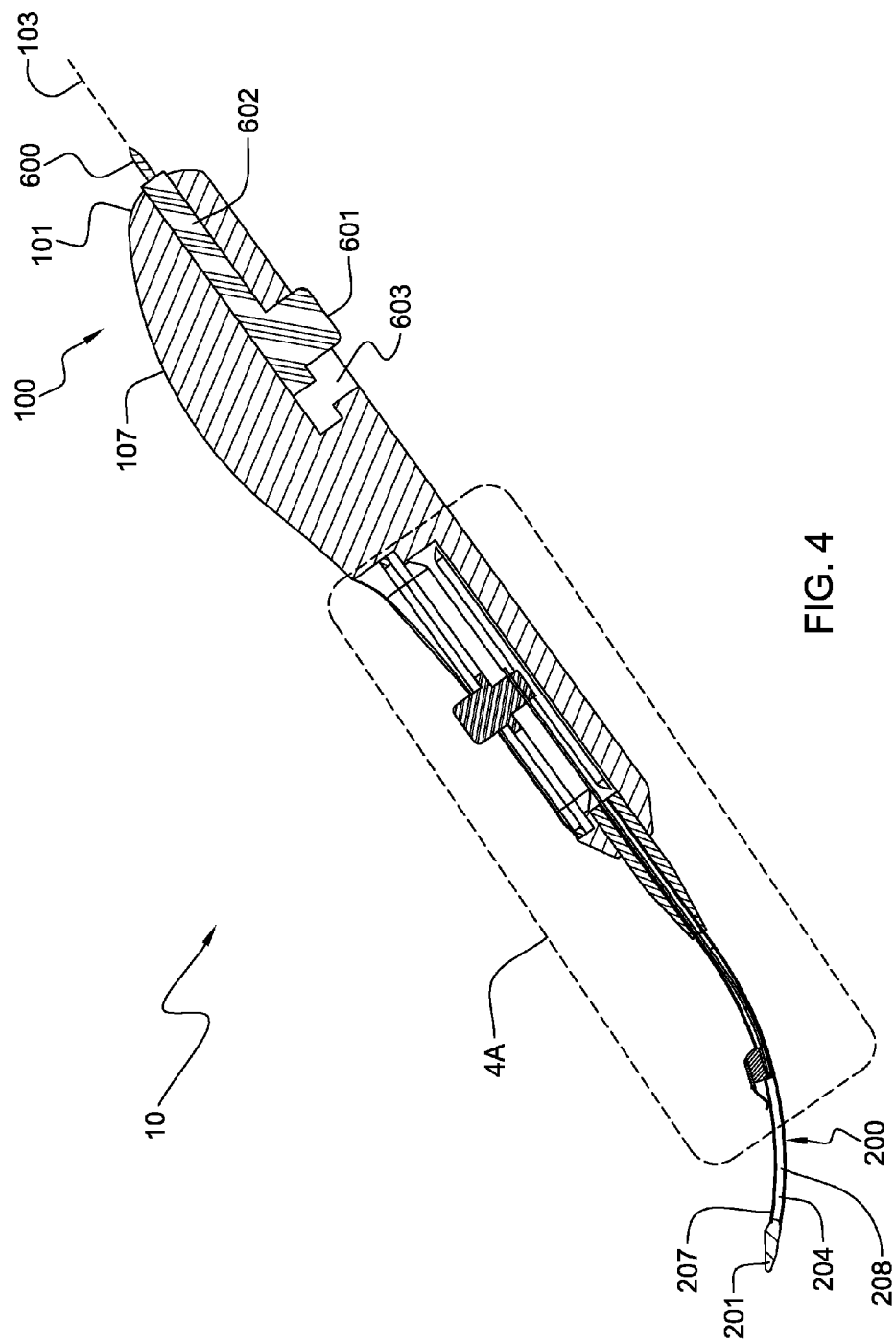
FIG. 4 is a cross-section, side elevational view of the surgical instrument of FIG. 1 taken along line 4-4, showing a coupling mechanism that operatively connects the blade member and the button member, in accordance with an aspect of the present invention.

FIG. 1 shows the general arrangement of a surgical instrument 10 for use to cut and release soft tissue within the human body, in accordance with an aspect of the present invention. Surgical instrument 10 includes generally a handle 100 having a proximal end 101 and a distal end 102 and a slot 104. Surgical instrument 10 further includes a tube 200 having a first end 201, a second end 202 and a slot 204 that extends along a longitudinal axis 203 and is disposed at least partially along the superior surface 207 of tube 200. As seen in FIG. 1, tube 200 is curvilinear, although it would be obvious to one skilled in the art that tube 200 may also be linear or straight. The arc of curvature 205 may be variable or changed in the event flexible material is used to construct tube 200 or fixed at a certain curvature for rigid material. Curve 205 functions to assist with the insertion of tube 200 into the surgical opening of a patient and facilitate continued advancement of tube 200 though the soft tissue of the patient to allow for appropriate positioning before the blade member 300 is operatively positioned. Further, as seen in FIGS. 1 and 4, tube 200 has a generally cylindrical cross-section, but it would be obvious to one skilled in the art that tube 200 could be comprised of one or more cross-sectional shapes, including, but not limited to rectangular, oval, I-beam or other shapes. Tube 200 is usually fabricated from a rigid material, such as stainless steel or another surgical steel, polyvinyl chloride (PVC), polytetrafluoroethylene (PTFE), expanded polytetrafluoroethylene (ePTFE), acryonitrile butadiene styrene (ABS) or any other suitable rigid metal or polymer material. Alternatively, tube 200 may be constructed from a flexible plastic or ductile/pseudo-elastic metal that has sufficient flexibility and strength to allow the surgeon to manually bend tube 200 and also have adequate rigidity to retain such a bend during the use of surgical instrument 10. Such flexibility of tube 200 may facilitate the proper placement of surgical instrument 10 with respect to the surgical site and the target soft tissue structure.

Figure 4A:
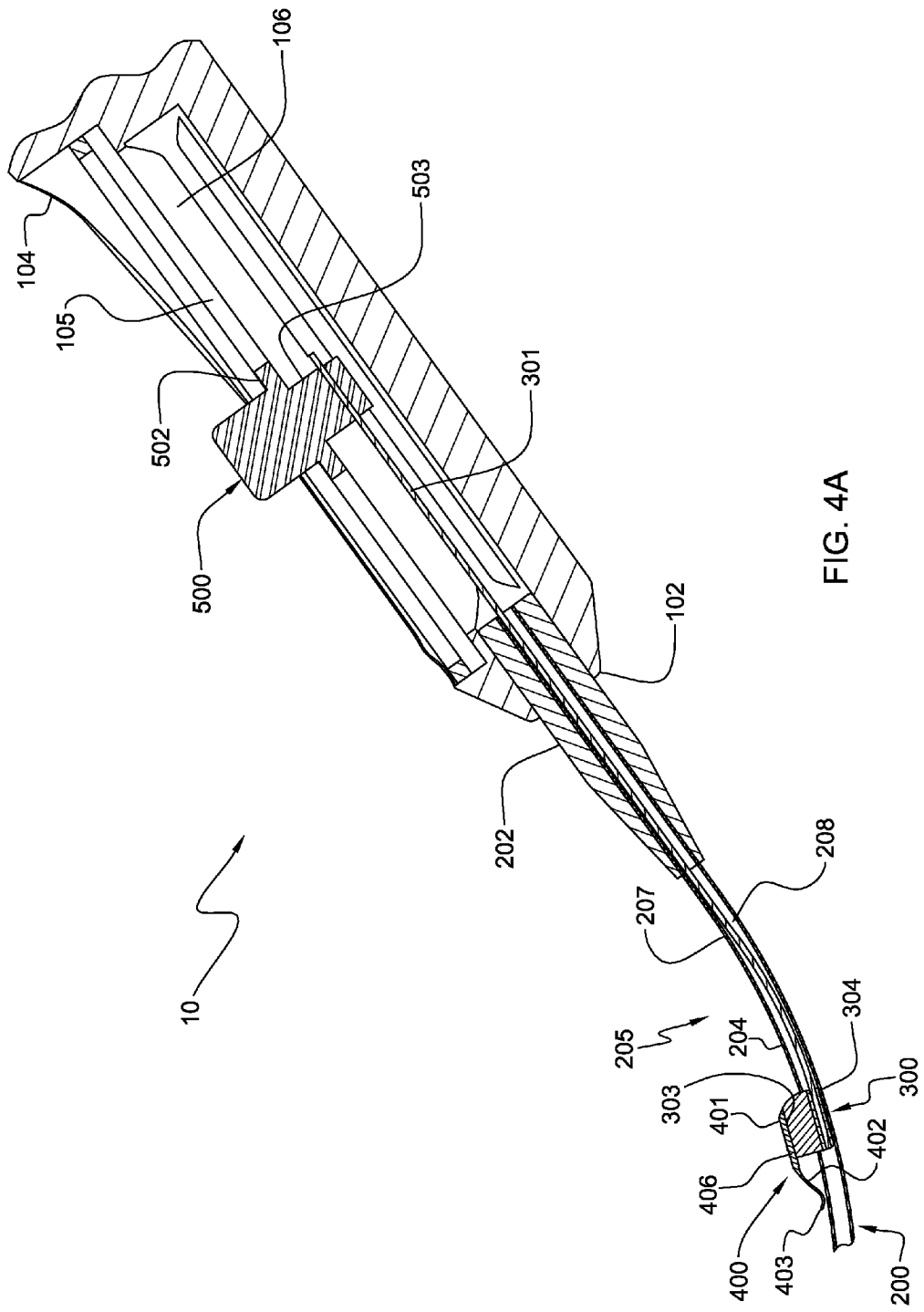
FIG. 4A is an enlarged cross-section, side elevational view of a portion of the surgical instrument of FIG. 1 taken along line 4-4, showing the blade member attached to the coupling mechanism that attaches to the button member, in accordance with an aspect of the present invention.

As shown in FIGS. 4 and 4A, tube 200 is generally hollow over its entire length to form an inner cavity 208 that is sized to accommodate a coupling mechanism 301 that connects blade member 300 to the button member 500 or more generally referred to as actuator. In operation, coupling mechanism 301 correspondingly slides within inner cavity 208 of tube 200 and the inner cavity 106 of handle 100 when button member 500 is moved either in a distal or proximal direction Inner cavities 208, 106 are constructed to receive various sizes of coupling mechanism 301 and allow for blade member 300 to slide along superior surface 207 of tube 200.

FIGS. 4 and 4A also show slot 204 that is sized to receive a portion of blade member 300 that connects to coupling mechanism 301. Slot 204 runs generally the entire length of tube 200, although it would be obvious to one skilled in the art to construct tube 200 with a slot that only partially extends over the length of tube 200. Slot 204 is oriented along longitudinal axis 203 providing for translation movement along the axis 203 when button member 500 actuates blade member 300. The width of slot 204 is toleranced to accommodate blade member 300 while maintaining minimal medial-lateral movement or toggle relative to tube 200 when blade member 300 is moved along longitudinal axis 203.

First end 201 of tube 200 is shown in FIG. 2 as a conical shape with a blunted tip. It is contemplated that the shape of first end 201 may be variable according to the end use of surgical instrument 10. Specifically, first end 201 may be conical shape as shown, a frustoconical shape, a bulbous shape, a beveled configuration, a rounded shape, a spherical shape, an elliptical shape or have a blunted end. The shaped first end 201 may be rigidly fixed to tube 200, or alternatively, detachably connected to allow for interchangement of the various shaped end pieces of first end 201. Having such modularity between tube 200 and first end 201 allows the surgeon to customize surgical instrument 10 for specific operative situations and purposes. Although not shown, it is well understood that when first end 201 is modular in design, the attachment mechanism between tube 200 and first end 201 may include threads, locking pins, spring clips, spring ball/catch or a twist lock. An alternative embodiment of tube 200 may also include a structure or detent mechanism positioned near first end 201 that may engage the blade member 300 and guard member 400 construct. Although not shown, such structure may be located on superior surface 207 and will function to either produce an audible sound or a tactile sensation to the surgeon when the blade member 300 and guard member 400 construct comes into contact with the structure on tube 200. This structure provides some form of sensory feedback to the surgeon indicating the distal position of the construct following insertion of tube 200 into the surgical opening.

As shown in FIG. 1, second end 202 functions to attach tube 200 to distal end 102 of handle 100. Second end 202 may rigidly attach tube 200 to handle 100, or alternatively, second end 202 may be configured to allow for detachment by the surgeon. Allowing for such interchangeability provides the surgeon with the ability to attach various lengths, shaped and sized tubes 200 in response to a presented surgical situation. Such modularity between tube 200 and handle 100 provides the surgeon with increased operative flexibility and customization. Although not shown, it is well understood by those skilled in the art that several attachment mechanism may be employed to operatively connect tube 200 and handle 100 by second end 202 including, threads, twist lock, locking pins, spring clips, spring balls or a spring catch.

In the depicted embodiment of FIG. 1, surgical instrument 10 may be entirely constructed of metal, plastic, or other rigid and sturdy materials and will be intended to be reusable. In an alternative embodiment, surgical instrument 10 may be designed to be single use and disposable. The reusable embodiment of surgical instrument 10 will generally be sterilized in any manner known to those of ordinary skill in the art between patients and, consequently, will generally be more economical over time than disposable devices. Constructing tube 200 out of a rigid, reusable material such as metal also provides for increased strength which will generally make tube 200 more resistant to bending or breaking in the event the surgeon needs to apply increased pressure or force to first end 201 in order to advance tube 200 within the surgical opening to perform the desired procedure.

It is further contemplated that because of the modularity design of surgical instrument 10 that various elements will be constructed from reusable materials while other elements are constructed from disposable materials. For example purposes only, handle 100 may be fabricated from metal, ABS or PVC while tube 200 is made from a disposable material, allowing the user to disconnect and discard tube 200 after a single use.

An embodiment of a surgical instrument kit is contemplated and described in more detail below. For example, the kit may include a reusable handle 100 with a series of various sized, angled/arced and shaped disposable assembled tube constructs with each construct including tube 200 with an inserted blade member 300, and attached coupling mechanism 301 and guard member 400. Other iterations of kit assemblies may include reusable handle-tube constructs with disposable blade members 300 and guard members 400. It would be well understood by one skilled in the art that several combinations and iterations of a surgical instrument kit, including kits that have other accessory surgical tools and miscellaneous surgical paraphernalia, could be assembled and would depend upon the surgical application and type of procedure in which the surgical instrument 10 would be used.

FIGS. 1, 4 and 4A further show handle 100 that includes proximal end 101, distal end 102 with longitudinal axis 103 extending between these two ends. Handle 100 also includes a slot 104 that is positioned on the superior surface 107 and extends generally parallel to longitudinal axis 103. Slot 104 is sized to receive button member 500 and accommodate translational movement of button member 500 along longitudinal axis 103.

As depicted in the cross-sectional views of FIGS. 4 and 4A, handle 100 includes an inner cavity 106 that is positioned directly adjacent to slot 104 and extends through distal end 102. The size and configuration of inner cavity 106 allows for the passage of coupling mechanism 301 and button member 500 Inner cavity 106 also includes at least two inner channels 105 running generally parallel to longitudinal axis 103 Inner channels 105 are configured to hold the outer flanges 502 of button member 500. Outer flanges 502 in cooperation with inner channels 105 stabilize button member 500 while button member 500 slides within slot 104 Inner channels 105 also function to keep button member 500 from rotating while being actuated. Although not shown, button member 500 may engage a structure within slot 104 or more specifically inner channel 105 that either generates a sound or a tactile sensation that provide the surgeon with feedback that button member 500 has been moved to the most distal position and correspondingly, blade member 300 and guard member 400 construct is now located at its most distal position relative to tube 200. FIGS. 4 and 4A further show button member 500 including a connection post 503. Connection post 503 extends from the inferior aspect of button member 500 and attaches to the proximal end of coupling mechanism 301. When in operation, button member 500 is actuated or slid within slot 104 by the surgeon, causing a corresponding sliding movement of blade member 300 within slot 204 of tube 200. Movement of button member 500 translates to direct movement of blade member 300 via coupling mechanism 301 that mechanically connects these two structures.

FIG. 4 further shows handle 100 having at its proximal end 101, a moveable cutting blade 600. Cutting blade 600 when not in use is fully retracted into a cavity 603 in order to avoid any injury to the surgeon when the surgeon is using surgical instrument 10 to release soft tissue using the other operative end of the device. Changing the position of cutting blade 600 is accomplished by actuating button 601 to unlock cutting blade 600 and permit it to extend from proximal end 101 through cavity 603. A connector 602 couples button 601 to cutting blade 600 with a spring catch or ball acting in conjunction with button 601 to secure cutting blade 600 either in the extended or retracted position.

As seen in FIG. 1, the outer surface of handle 100 is usually configured to fit into the hand of the surgeon. Various non-slip surface textures and shaping may be performed/applied to superior surface 107 to ensure acceptable comfort and dexterity for the surgeon when the device is being used.

FIG. 3 shows guard member 400 coupled to blade member 300. As shown, blade member 300 includes a cutting edge 302 disposed along the distal portion of blade member 300. Cutting edge 302 as shown is oriented generally perpendicular relative to tube 200 and is defined by a straight line. Cutting edge 302 is usually fabricated from a metallic material, although a rigid polymer may be used. It would be understood by one skilled in the art that cutting edge 302 may also be positioned at an acute angle relative to tube 200. In addition, cutting edge 302 instead of being straight may also be defined by an angle or by an arc relative to the sagital plane or longitudinal axis to facilitate cutting and releasing any soft tissue that is engaged. Further, cutting edge 302 may be modular relative to blade member 300 to allow for interchangeability in the event of a changed clinical situation or surgical procedure. Connection mechanisms between a modular cutting edge 302 and blade member 300 are well known in the art. Typically, connected to the superior surface 303 of blade member 300 is the hood portion 401 of guard member 400. As seen in cross-sectional view FIG. 4A, the inferior portion 304 of blade member 300 is also connected to coupling member 301 that is then connected to button member 500. As disclosed above, coupling mechanism 301 connects button member 500 to blade member 300 and passes along inner cavities 106, 208. Coupling mechanism 301 operates to correspondingly move blade member 300 along slot 204 of tube 200 when button member 500 is moved. It is not shown, but is contemplated that coupling mechanism 301 may be detachable from either button member 500, or alternatively, from blade member 300, thus allowing blade member 300 to be modular in design and allow for interchangeability to address various clinical conditions and surgical procedures if different cutting edge sizes, angulations or shapes are necessary while keeping tube 200 and handle 100 construct intact.

Guard member 400 as seen in FIGS. 3 and 4A includes hood portion 401, a capture portion and a distal tip 403. Generally, the inferior surface of hood portion 401 is rigidly attached to superior surface 303, although it is contemplated that an alternative embodiment of the invention may have hood portion 401 that is detachable from superior surface 303 allowing for interchangeability between various sizes and configurations of guard member 400 and blade member 300. Extending from and slanting in an inferior direction is capture portion 402. Capture portion 402 includes a width 404 that is configured to entrap or pressingly engage tissue between an inferior surface 405 of capture portion 402 and superior surface 207 of tube 200. When in operation, the superior surface 406 of capture portion 402 functions to move or displace surrounding tissue away from blade member 300 when tube 200 is inserted into a surgical opening and blade member is moved along tube 200 to its operative position before cutting the target soft tissue. Superior surface 406 also functions to protect adjacent structures (e.g., nerves, vascular structures) from cutting edge 302. As shown in FIG. 3, superior surface 406 of capture portion 402 is generally flat, although not shown, it should be understood that superior surface 406 may also be angular or shaped in a plow-like configuration to facilitate tissue movement and protection. Additionally, it would be well understood by one skilled in the art that width 404 may also be varied or tapered depending on the surgical procedure that may be performed with surgical instrument 10. Varying width 404 may be accomplished by having a modular capture portion 402 that can be detached from hood portion 401. Width 404 may also be changed by having capture portion 402 be expandable in the medial-lateral dimension.

As shown in FIGS. 3, 4 and 4A, guard member also include distal tip 403 that is typically fabricated from a flexible material. Distal tip 403 is configured to be an upward projecting arc shaped element that is configured similar to a ski tip. Alternative configurations of distal tip 403 are contemplated to include upward oriented chamfers, bevels, wedges, cones, tapers, spheres and drifts. The purpose of distal tip 403 is to facilitate the passage of soft tissue beneath the construct to allow for engagement with cutting edge 302 of blade member 300. FIG. 3 depicts distal tip 403 as being integral to capture portion 402, although an alternative embodiment of the invention may include a distal tip 403 that can be uncoupled from capture portion 402 and, thus be removable and modular to allow the surgeon to interchange various different tip configurations that best suits a presented clinical or surgical application. Methods of connecting distal tip 403 to capture portion 402 are well know in the art and may include press fit, spring balls, spring catches and locking pins.

Referring now to FIGS. 5-9, one example of a method for releasing soft tissue in the case of trigger finger will now be discussed in conjunction with the above-illustrated embodiment of the surgical instrument. As seen in FIG. 5, the method includes surgically creating an incision 700 just distal to the metacarpal phalangeal joint crease in the palm. Proximal cutting blade 600 may be used to create incision 700. It should be noted that the orientation of incision 700 as shown in FIGS. 5 and 6 is transverse, but such orientation may be changed at the discretion of the surgeon. The method further includes inserting surgical instrument 10, or more specifically, tube 200 through incision 700 as shown in FIG. 6. As disclosed above, surgical instrument 10 generally includes handle 100 with proximal end 101 and distal end 102, tube 200 with first end 201 and second end 202, and longitudinal axis 203. First end 201 is constructed to facilitate the insertion of tube 200 through incision 700 with second end 202 being configured to attach or detachably couple to distal end 102 of handle 100. In addition, surgical instrument 10 to be used in the method may include blade member 300 that slidingly engages tube 200 and is moveable relative to tube 200 along longitudinal axis 203.

Figure 7:
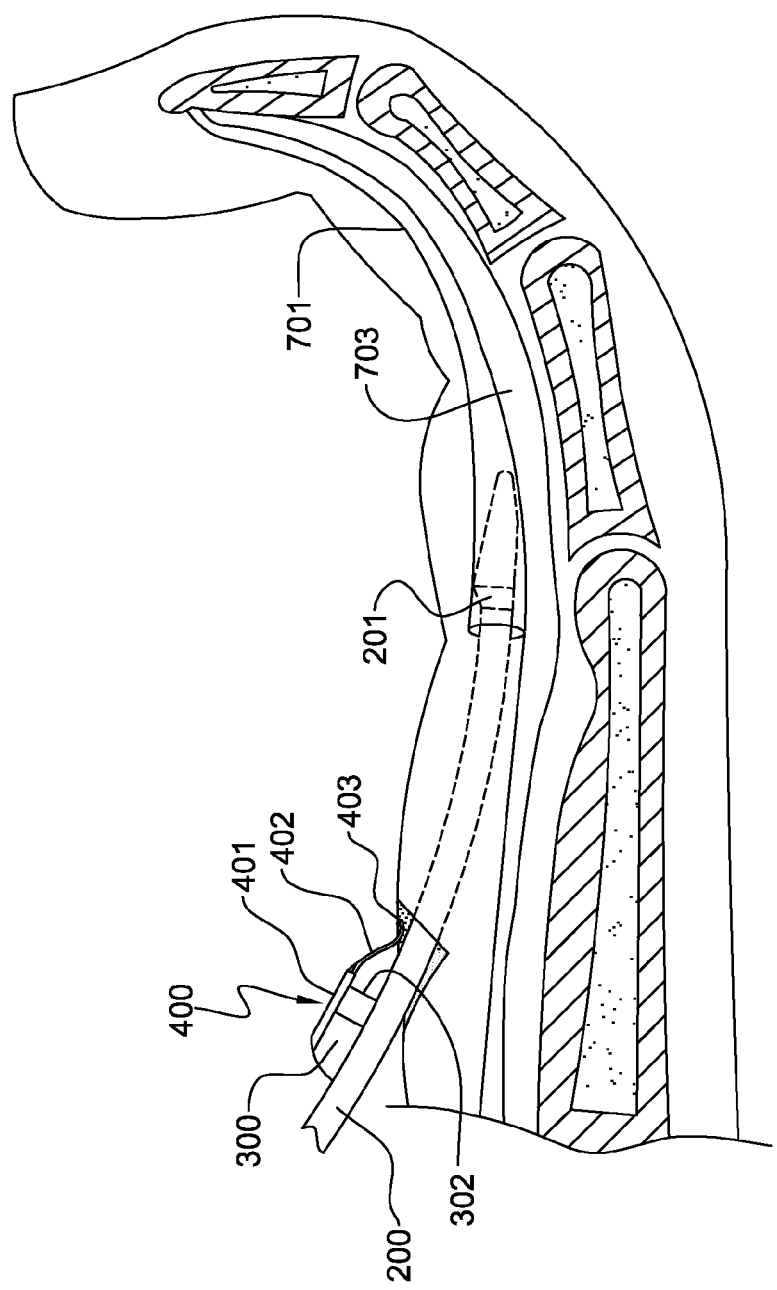
FIG. 7 is a cross-sectional view through the patient's finger of the inserted surgical instrument of FIG. 1, showing the first end of the tube between a tendon sheath and a tendon, in accordance with an aspect of the present invention.

As shown in the cross-sectional view of FIG. 7, the method also includes advancing tube 200 within incision 700 with first end 201 bluntly entering the flexor tendon sheath 701 to position first end 201 adjacent to the target soft tissue. When tube 200 has been advanced through flexor tendon sheath 701 to the proximal end of the A1 pulley, the method will further include actuating or moving blade member 300 along longitudinal axis 203 to contact and engage the soft tissue and place blade member 300 or more specifically, cutting edge 302 in operable position relative to the A1 pulley structure.

Figure 8:
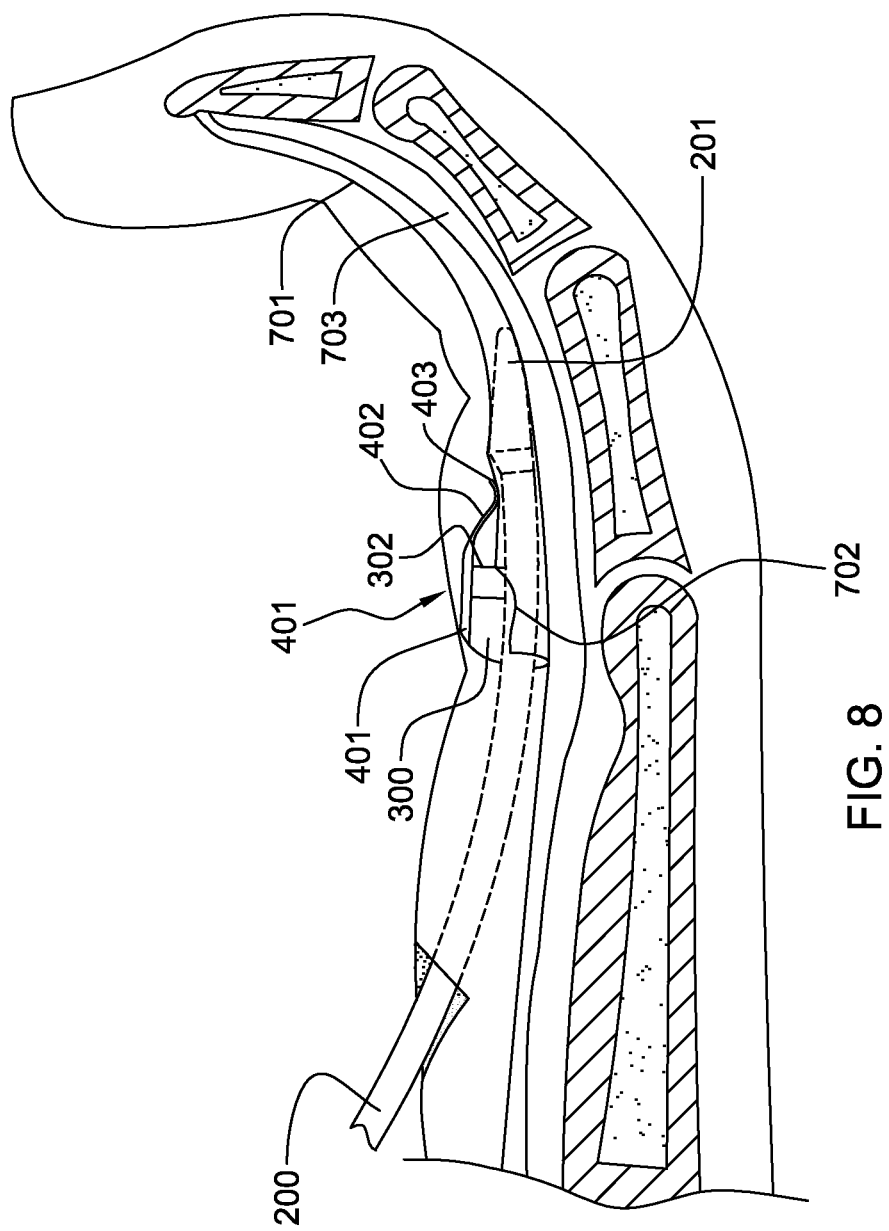
FIG. 8 is a cross-sectional view through the patient's finger of the inserted surgical instrument of FIG. 1, showing the first end of the tube between the tendon sheath and the tendon with the capture portion of the guard member engaging the tendon sheath as the blade member cuts the tendon sheath to release the soft tissue, in accordance with an aspect of the present invention.

Cross-sectional view FIG. 8 shows tube 200 in final position with blade member 300 in operable position relation to A1 pulley 702. Blade member 300 is then moved distally to the distal end of the A1 pulley 702 slicing off a section of the pulley and releasing the soft tissue or flexor tendon sheath 701. It should be noted that when advancing tube 200 within flexor tendon sheath 701, guard member 400 and more specifically, hood portion 401 and capture portion 402 push or move surrounding soft tissue and other structures away from flexor tendon sheath 701 and blade member 300 to prevent damage to the nerves, veins, and arteries that are adjacent to the flexor tendon 703 and flexor tendon sheath 701. As seen in FIG. 8, capture portion 402 functions to trap a section of flexor tendon sheath 701 to allow cutting edge 302 to divide a section, or the entire length of flexor tendon sheath 701 depending on the degree of constriction or stenosis presented.

Although not shown, after a section of A1 pulley 702 has been cut, or alternatively, A1 pulley has been divided, the method includes extracting and removing surgical instrument 10 from the patient's finger, followed by closing the incision using a suture or closure tape.

As disclosed above, the embodiment of surgical instrument 10 described herein may be modular in design, thereby allowing the operating surgeon to choose from a surgical instrument kit that includes a multiple of differently sized and shaped elements, including handles 100, tubes 200, blade members 300 and guard members 400. The surgical instrument kit provides the operating surgeon with the flexibility to mix and match appropriate sized and configured elements of the surgical instrument to best address the presented clinical situation and surgical procedure. The kit typically is comprised of a series or plurality of surgical instruments with each surgical instrument 10 including handle 100, tube 200, button member 500, blade member 300 and guard member 400. The structure and geometrical dimensions of the above elements of surgical instrument 10 are much the same as those designated by the same numeral which were described above in reference to FIGS. 1-4A. For the sake of brevity, said elements will not be further discussed at this point.

Generally, the surgical instrument kit may be comprised of various lengths, shapes or curvatures and cross-sectional sizes and shapes of tubes 200. Each tube 200 will have first and second ends 201, 202 allowing for attachment to distal end 102 of handle 100. It is further contemplated that the surgical instrument kit may include a plurality of different sized and configured blade members 300 and corresponding guard members 400 with a modular coupling mechanism that allows for easy placement and attachment to tube 200 and handle 100. Having a plurality of differing sized and configured blade members 300 and corresponding guard members 400 allows the operating surgeon the ability to pick a cutting blade that most closely matches the need for a specific procedure. Additionally, the surgical instrument kit will have a plurality of handles 100. Again, the plurality of handles 100 gives the operating surgeon the ability to attach whatever sized handle 100 and button member 500 is appropriate for the surgical procedure to be performed. Each of the plurality of handles 100 may be sized and shaped differently to best fit the needs of the operating surgeon.

Having a surgical instrument kit that includes modular elements of the surgical instrument 10 can provide certain benefits including decreased institutional costs while providing to the operating surgeon the ability to customize an instrument for a specific clinical application while performing the surgical procedure.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A method for releasing soft tissue within a patient, the method comprising:
   surgically creating an opening on skin of a patient, wherein the opening is proximate to the soft tissue to be released;
   inserting a surgical instrument into the opening, the surgical instrument comprising:
   a handle having proximal and distal ends, and a longitudinal axis extending therebetween;
   a tube having a first end and a second end, and a longitudinal axis extending therebetween and a slot disposed at least partially along a superior surface of the tube and extending along the longitudinal axis, the first end being configured to facilitate the insertion of the surgical instrument into the opening on the skin of the patient and the second end being configured to couple to the distal end of the handle;
   a blade member having a cutting edge, the blade member being configured to slidingly engage within the slot of the tube with the cutting edge exterior to the tube and is moveable relative to the tube along the longitudinal axis to release soft tissue; and
   a guard member, the guard member comprising a hood portion and a capture portion, wherein when an inferior surface of the hood portion is connected to a superior surface of the blade member, the capture portion is positioned distal to the cutting edge of the blade member and extends from and slants in an inferior direction from the hood portion to displace surrounding tissue when the blade member is actuated along the longitudinal axis of the tube within the slot, and the guard member moves with the blade member following insertion of the surgical instrument into the opening on the skin of the patient;

advancing the tube of the surgical instrument into the opening on the skin of the patient to position the first end of the tube adjacent to the soft tissue;

actuating the blade member along the longitudinal axis of the tube to engage the soft tissue and place the blade member in operable position; and when the blade member is in operable position, holding the tube in a position adjacent to the soft tissue and sliding the blade member within the slot to release the soft tissue.

2. The method of claim 1, wherein the capture portion of the guard member is fabricated from a flexible material to pressingly engage soft tissue structures between the capture portion and the tube when the blade member is actuated along the longitudinal axis of the tube following insertion of the surgical instrument into the opening on the skin of the patient.

3. The method of claim 1, wherein the capture portion further comprises a distal tip, the distal tip being configured as at least one of an arc shape, a chamfer, a taper, a cone, a wedge, a spherical shape, and a bevel to facilitate the passage and engagement of soft tissue structures when the blade member is actuated following insertion of the surgical instrument into the opening on the skin of the patient.

4. The method of claim 1, wherein the tube is curved along its longitudinal axis to facilitate the insertion and advancement of the surgical instrument into the opening on the skin of the patient.

5. The method of claim 1, wherein the surgical instrument further comprises an actuator, wherein the actuator is in a slot in the handle and the slot in the handle facilitates movement of the actuator therein.

6. The method of claim 5, wherein the actuator is operationally connected to the blade member, whereby actuation of the actuator moves the blade member along the longitudinal axis of the tube until the blade member is in operable position to cut and release the soft tissue.

7. The method of claim 1 further comprising:
extracting the surgical instrument from the opening on the skin of the patient after cutting the soft tissue; and
surgically closing the opening on the skin of the patient following the removal of the surgical instrument.

8. A method for releasing soft tissue within a patient, the method comprising:

surgically creating an opening on skin of a patient, wherein the opening is proximate to the soft tissue to be released;

inserting a surgical instrument into the opening, the surgical instrument comprising:

a handle having proximal and distal ends, and a longitudinal axis extending therebetween;

a tube having a first end and a second end, and a longitudinal axis extending therebetween and a slot disposed at least partially along a superior surface of the tube and extending along the longitudinal axis, the first end being configured to facilitate the insertion of the surgical instrument into the opening on the skin of the patient and the second end being configured to couple to the distal end of the handle;

a blade member having a cutting edge, the blade member being configured to slidingly engage within the slot of the tube with the cutting edge exterior to the tube and is moveable relative to the tube along the longitudinal axis to release soft tissue; and a guard member, the guard member comprising a hood portion and a capture portion, wherein when an inferior surface of the hood portion is connected to a superior surface of the blade member, the capture portion is positioned distal to the cutting edge of the blade member and extends from and slants in an inferior direction from the hood portion to displace surrounding tissue when the blade member is actuated along the longitudinal axis of the tube within the slot, and the guard member moves with the blade member following insertion of the surgical instrument into the opening on the skin of the patient;

advancing the tube of the surgical instrument into the opening on the skin of the patient to position the first end of the tube adjacent to the soft tissue;

actuating the blade member along the longitudinal axis of the tube to engage the soft tissue and place the blade member in a first position; and cutting the soft tissue with the blade member to release the soft tissue by moving the blade member from the first position to a second position.

9. The method of claim 8, further comprising:
extracting the surgical instrument from the opening on the skin of the patient after cutting the soft tissue.

10. The method of claim 9, further comprising:
surgically closing the opening on the skin of the patient following the extraction of the surgical instrument.

* * * * *

UNITED STATES PATENT AND TRADEMARK OFFICE
CERTIFICATE OF CORRECTION

| | | |
|---|---|---|
| PATENT NO. | : 9,028,516 B2 | Page 1 of 1 |
| APPLICATION NO. | : 14/054560 | |
| DATED | : May 12, 2015 | |
| INVENTOR(S) | : Palmer et al. | |

It is certified that error appears in the above-identified patent and that said Letters Patent is hereby corrected as shown below:

On the Title Page

Item (73): Delete "Del Palma Orthopedics" and insert --Del Palma Orthopedics, LLC--

Signed and Sealed this
Twentieth Day of October, 2015

Michelle K. Lee
*Director of the United States Patent and Trademark Office*